United States Patent [19]
Ryan et al.

[11] Patent Number: 6,001,106
[45] Date of Patent: Dec. 14, 1999

[54] SYSTEM FOR TENSIONING LIGAMENT GRAFTS

[75] Inventors: James P. Ryan, Amherst; Thomas V. Moser, Bedford, both of N.H.

[73] Assignee: M & R Medical, Inc., Bedford, N.H.

[21] Appl. No.: 08/922,707

[22] Filed: Sep. 3, 1997

[51] Int. Cl.⁶ .................................................. A61B 17/56
[52] U.S. Cl. .............................. 606/102; 606/88; 623/13
[58] Field of Search ............................... 606/102, 96, 97, 606/98, 86, 88, 72, 73; 623/13

[56] References Cited

U.S. PATENT DOCUMENTS

| | | |
|---|---|---|
| Re. 34,762 | 10/1994 | Goble et al. . |
| 1,347,579 | 7/1920 | Henrikson . |
| 1,822,352 | 9/1931 | Laursen . |
| 2,337,629 | 12/1943 | Shortell . |
| 2,516,079 | 7/1950 | Shortell . |
| 2,590,498 | 3/1952 | Bomberger . |
| 3,016,741 | 1/1962 | Kulp . |
| 3,432,930 | 3/1969 | Ljungberg . |
| 3,696,667 | 10/1972 | Foster et al. . |
| 3,896,500 | 7/1975 | Rambert et al. . |
| 3,953,896 | 5/1976 | Treace . |
| 3,973,277 | 8/1976 | Semple et al. . |
| 3,976,060 | 8/1976 | Hildebrandt et al. . |
| 4,024,860 | 5/1977 | Chelnokov et al. . |
| 4,050,464 | 9/1977 | Hall . |
| 4,102,339 | 7/1978 | Weber et al. . |
| 4,220,146 | 9/1980 | Cloutier . |
| 4,246,660 | 1/1981 | Wevers . |
| 4,312,343 | 1/1982 | LeVeen et al. . |
| 4,317,377 | 3/1982 | Wrinkle . |
| 4,364,389 | 12/1982 | Keller . |
| 4,501,266 | 2/1985 | McDaniel . |
| 4,712,542 | 12/1987 | Daniel et al. . |
| 4,772,286 | 9/1988 | Goble et al. . |
| 4,927,421 | 5/1990 | Goble et al. . |
| 4,960,420 | 10/1990 | Goble et al. . |
| 4,997,433 | 3/1991 | Goble et al. . |
| 5,037,426 | 8/1991 | Goble et al. . |
| 5,137,514 | 8/1992 | Ryan . |
| 5,147,362 | 9/1992 | Goble . |
| 5,393,302 | 2/1995 | Clark et al. . |
| 5,411,506 | 5/1995 | Goble et al. . |
| 5,423,828 | 6/1995 | Benson ..................................... 606/102 |
| 5,507,750 | 4/1996 | Coble et al. . |
| 5,562,668 | 10/1996 | Johnson . |
| 5,630,820 | 5/1997 | Todd ......................................... 606/90 |
| 5,800,438 | 9/1998 | Tuke et al. ................................ 606/90 |

FOREIGN PATENT DOCUMENTS 0280572  8/1988  European Pat. Off. .

OTHER PUBLICATIONS

Author unknown;"Instruments for ACL Reconstruction—Isometry Instruments"; Date Unknown; page unknown; publisher unknown.

Nabors et al; "Anterior Cruciate Ligament Graft Tensioning in Full Extension"; 1995; pp. 488–492; The American Journal of Sports Medicine, vol. 23, No. 4.

Burks et al; "Determination of Graft Tension BEfore Fixation in Anterior Cruciate Ligament Reconstruction" and "Cruciate Graft Tensioning"; 1988; pp. 260–266 and pp. 57–60; MEDmetric Corporation.

The American Journal of Sports Medicine, vol. 23, No. 4 Burns et al; "The Effect of Femoral Tunnel POsition and Graft Tensioning Technique on Posterior Laxity of the Posterior Cruciate Ligament–Reconstructed Knee"; 1995; pp. 424–430.

(List continued on next page.)

*Primary Examiner*—Michael Buiz
*Assistant Examiner*—David O. Reip
*Attorney, Agent, or Firm*—Hayes Soloway Hennessey Grossman & Hage PC

[57] ABSTRACT

Apparatus for tensioning a ligament graft includes a hydraulic tensioning cylinder with a piston having a distal end for holding and affixing, relative to the distal end of the piston, a free end of a ligament graft, where the other end of the ligament graft is affixed to a patient. An inflation device, in hydraulic communication with a cylinder, moves the piston to tension the graft.

6 Claims, 7 Drawing Sheets

OTHER PUBLICATIONS

Belby III et al; The Effects of Graft Tensioning on the Laxity and Kinematics of the Anterior Cruciate Ligament Reconstructed Knee; 1991; pp. 257–266; The Journal of Arthroscopic and Related Surgery 7(3).

Gertel et al; "Effect of anterior cruciate ligament graft tensioning direction, magnitude, and flexion angle on knee biomechanics"; 1993; pp. 572–581; The American Journal of Sports Medicine, vol. 21, No. 4.

Vergis et al; "Graft Failure in Intra–Articular Anterior Cruciate Ligament Reconstructions: A Review of the Literature"; 1995; pp. 312–321; Arthroscopy: The Journal of Arthroscopic and Related Surgery, vol. 11, No. 3 (Jun.).

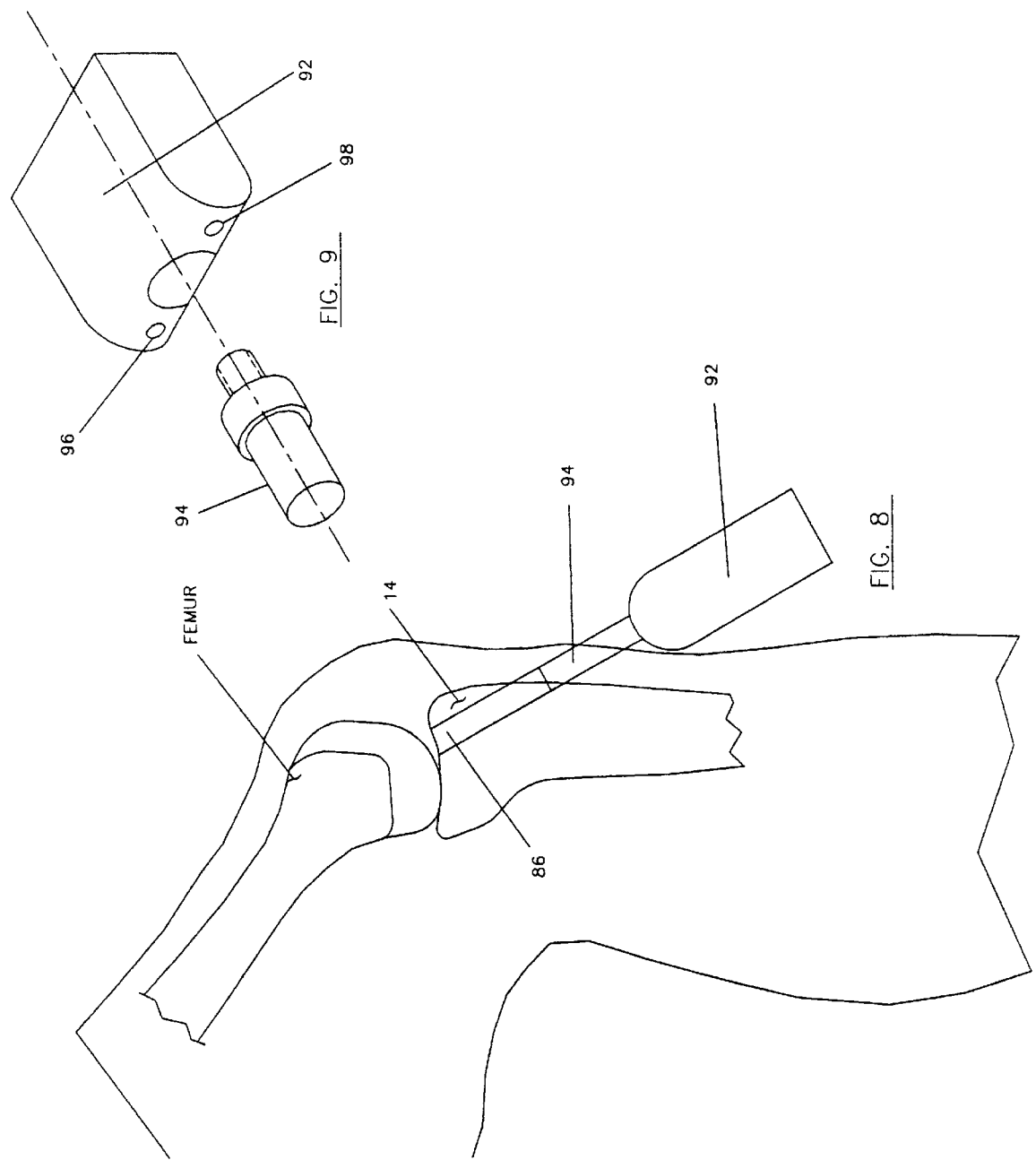

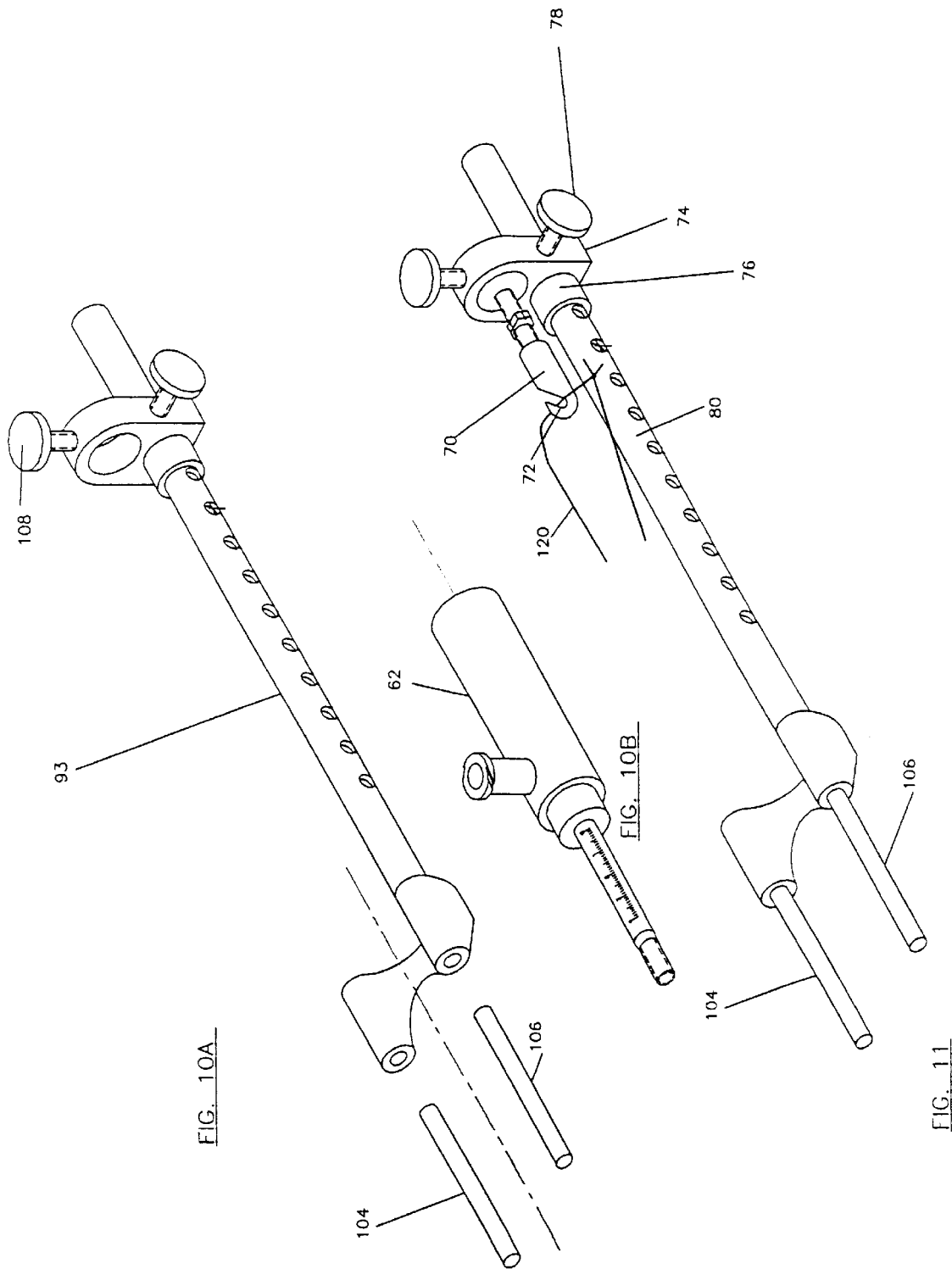

SYSTEM FOR TENSIONING LIGAMENT GRAFTS

BACKGROUND OF THE INVENTION

1. Field of the Invention

The present invention relates to surgical devices and methods for adjusting tension of ligament grafts. The invention has particular utility in connection with establishing ligament graft tension in knee surgery applications, and will be described in connection with such utility, although other utilities are contemplated.

2. Description of the Prior Art

Treatment of knee instability due, for example, to rupture of the anterior cruciate ligament has been a mixture of ligament repair, augmentation or substitution by tendon transfer. The most common technique at the present time is the use of an autogenous patella tendon graft with bone harvested from the patella and the tibial tuberosity. The patella tendon graft and bone plugs are fed into tunnels within the femur and tibia and secured at each end.

Successful tendon graft surgery is dependent on several factors including graft selection, tunnel placement, isometric placement, bone preparation, fixation devices, correct tensioning of the graft, and post-surgical rehabilitation, all of which have been thoroughly studied. All of the above factors are highly critical, and any variation from optimal control can result in graft failure. By way of example, theoretically, isometric placement is possible where the ligament remains at the same tension throughout the range of knee flexion and extension. However, this is difficult to achieve in practice. Many recent developments have attempted to define the isometric points for insertion of the drill and have demonstrated the effect of incorrect placement.

For the ligament to be functional, it not only has to be inserted isometrically, but it has to be correctly tensioned in order to allow a full range of motion. Various techniques have been developed for determining correct graft tensioning during a patella tendon reconstruction, none of which have been completely satisfactory since existing techniques do not permit measurement through full range of motion. In particular, excessive graft tension has been found to be detrimental to success in a continuous passive motion. Any graft material that is highly tensioned will be more subject to abrasion at the bony edges of tunnels or the notch and also subject to more frequent fixation failure. Thus, the importance for correct tensioning. Moreover a significant variable that has received little attention is the precise preloader tension applied to the graft before fixation. Another technical problem is to ensure that once proper tension on the graft is set, that the tension is maintained, without change, during fixation of the ends of the this ligament. Moreover, no method is believed to be currently available which permits tension to be incrementally increased while the range of motion and stability is continuously examined.

It is, accordingly, an object of the present invention to provide the system, i.e. method and apparatus which overcomes the aforesaid and other disadvantages of the prior art. Another object of the present invention is to provide the method and apparatus which is uniquely suited for establishment of proper skeletal referenced ligament graft tension. It is a specific object of the invention to provide a method and apparatus for establishing proper skeletal referenced ligament graft tension and fixation of a cruciate ligament graft during knee surgery.

SUMMARY OF THE INVENTION

The present invention provides a method and apparatus for ligament graft tensioning. The invention includes a measuring system for measuring elongation response of a graft ligament, and a graft tensioning device which includes a hydraulic tensioning cylinder having a piston having a distal end for holding and fixing, relative to the distal end of the piston, the free end of the ligament graft. An inflation device, in hydraulic communication with the cylinder, is provided for moving the cylinder relative to the piston to tension the graft in accordance with predetermined parameters. A pressure gauge on the inflation device provides a direct readout representative of the tension applied to the ligament graft. The invention in another aspect also provides a drill guide which works in cooperation with the graft tensioning device to align and support the device.

Still other objects and advantages of the present invention will become apparent from consideration of the following description, taken in connection with the accompanying drawings, wherein like numerals depict like parts and wherein:

BRIEF DESCRIPTION OF THE DRAWINGS

FIG. 8 is a perspective view of the sagittal section of the tibia, with the drill guide of the present invention operatively positioned in accordance with one step of the process of the present invention;

FIG. 9 is an exploded perspective view, showing details of the drill guide of FIG. 8;

FIGS. 10A and 10B are perspective views of cylinder and cylinder tensioning guide of the present invention;

FIG. 11 is a side elevational view showing details of the tensioning device of the present invention.

BRIEF DESCRIPTION OF THE PREFERRED EMBODIMENTS

Figure 1:
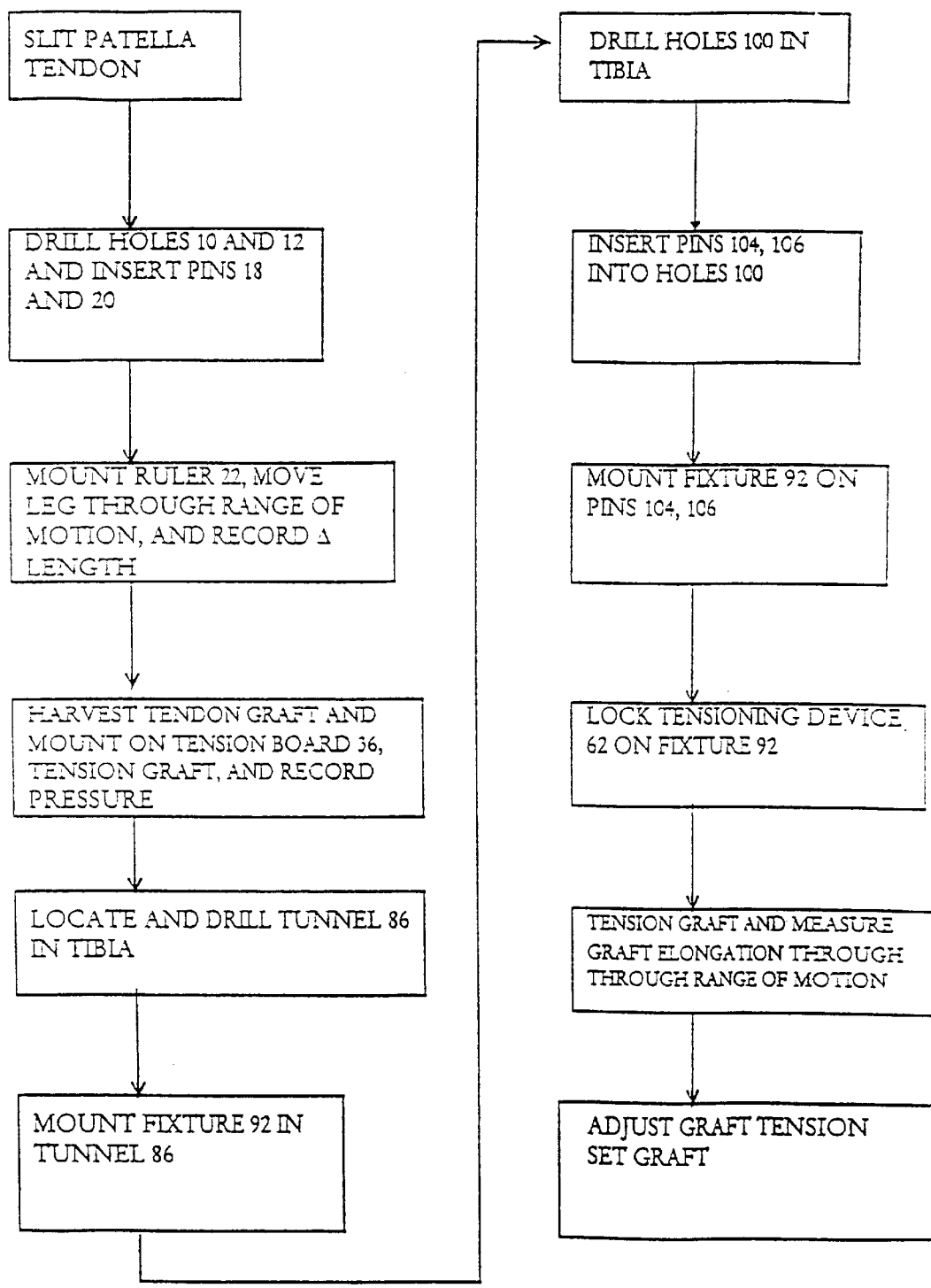
FIG. 1 is a side elevational view, schematically illustrating a femur-to-tibia ligament graft reconstruction process in accordance with a preferred embodiment of the subject invention.
Figure 2A:
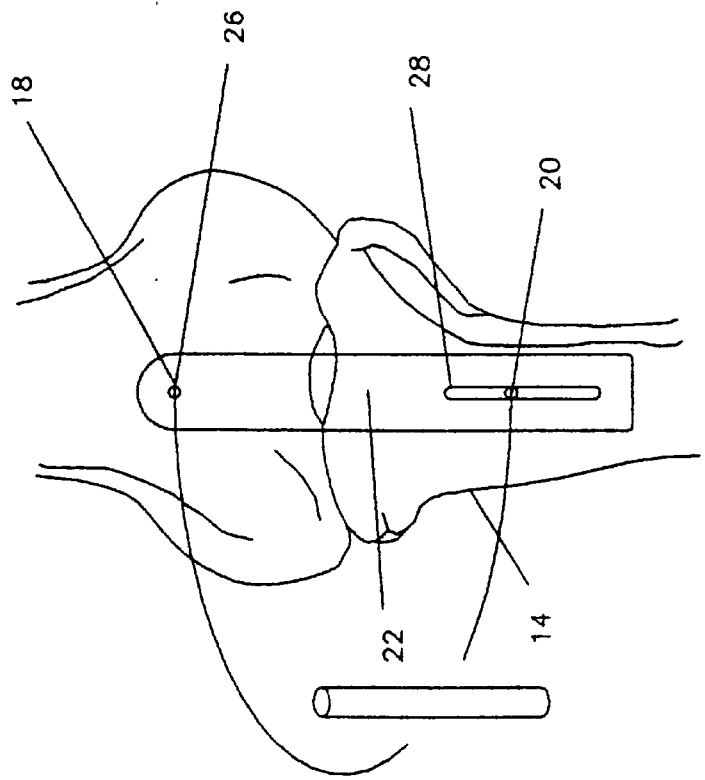
FIG. 2A is a top plan view of the sagital section of the tibia and femur with the range of motion ruler operatively positioned in accordance with one step of the process of the present invention.
Figure 2B:
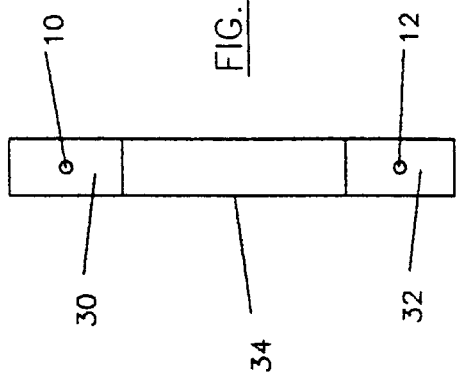
FIG. 2B is a top plan view of a ligament graft harvested in accordance with another step of the process of the present invention.
Figure 4:
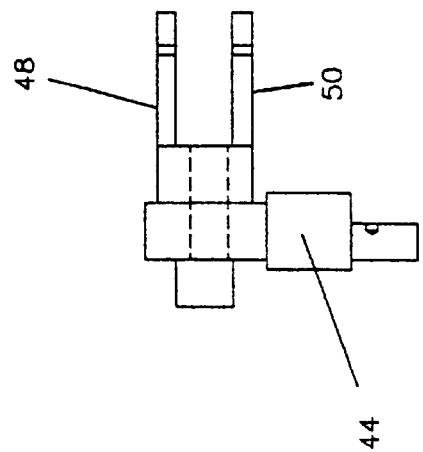
FIG. 4–7 show details of elements of the tensioning board and tensioning cylinder of FIG. 3.
Figure 3:
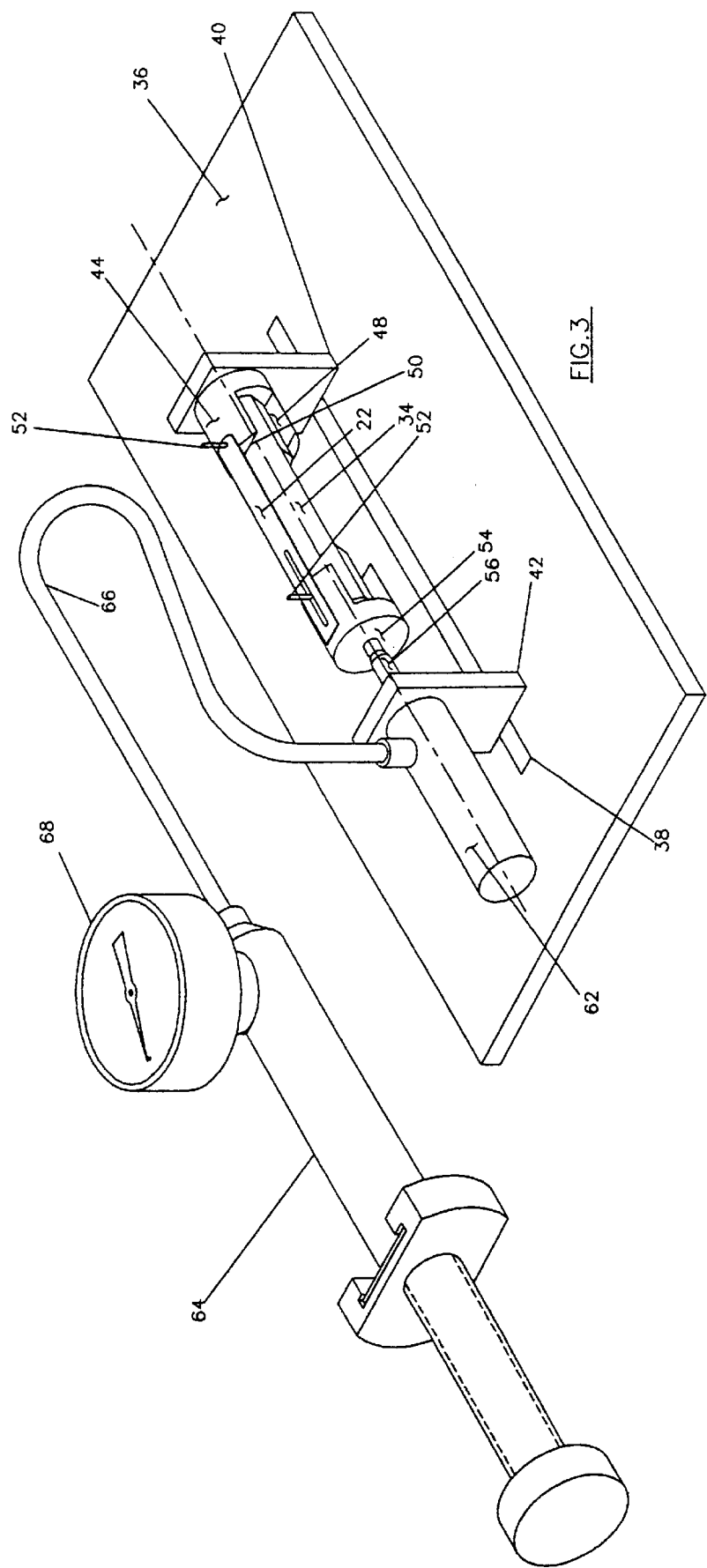
FIG. 3 is a perspective view showing the graft and range of motion ruler mounted on a tensioning board in combination with a hydraulic graft tensioning device made in accordance with the present invention, in another step of the process of the present invention.

Referring to the drawings, referring in particular to FIGS. 1–2B, the first step in the process of the present invention is to determine the normal range of elongation of the ligament graft once an incision is made to expose the patella tendon. Accordingly, the first step involves slitting the center third of the patient's patella tendon. Holes 10 and 12 then are drilled into the heads of the patient's tibia 14 and patella 16, respectively, adjacent the ends of the slit tendon. A pair of pins 18 and 20 are press-fitted into holes 10 and 12, respectively, and an elongate slotted flexible ruler 22 is fitted over pins 18 and 20. As can be seen in FIG. 2A, ruler 22, which includes marked indicia corresponding to length measurements, includes a round hole 26 for accommodating pin 18, and an elongate slot 28 sized to accommodate pin 20.

The patient's knee is then put through a full range of motion, and linear measurements taken at 0°, 45°, 90°, and full flexion, and the linear measurements recorded in Table I as described hereinafter. Thereafter, the ruler 22 and pins 18 and 20 are removed, and the harvesting of the tendon graft is completed, with the slit tendon removed attached to a femoral bone block 30 encompassing hole 10, and a tibial bone block 32, encompassing hole 12.

Referring to FIGS. 3–7, the harvested graft 34 is then mounted on a tensioning board 36. Tensioning board 36 includes an elongate slot 38 into which there are mounted sleds 40 and 42. A fixture 44, mounted on a sled 40, includes an opening defined by a pair of tangs 48 and 50. A removable pin 52 is mounted in fixture 44, extending through a through-hole in tang 50, through hole 10 in bone block 30, and into a blind hole in tang 48. As seen in particular in FIG. 3, one end of the harvested ligament graft 34 and one end of ruler 22 are mounted on pin 52.

Figure 5:
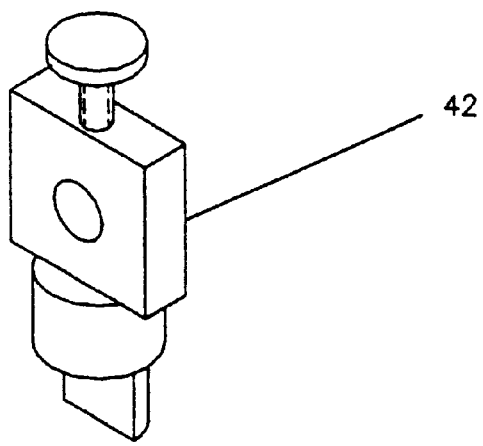
Figure 6:
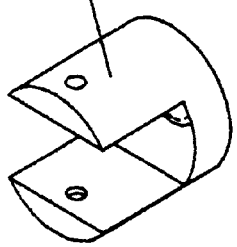
Figure 7:
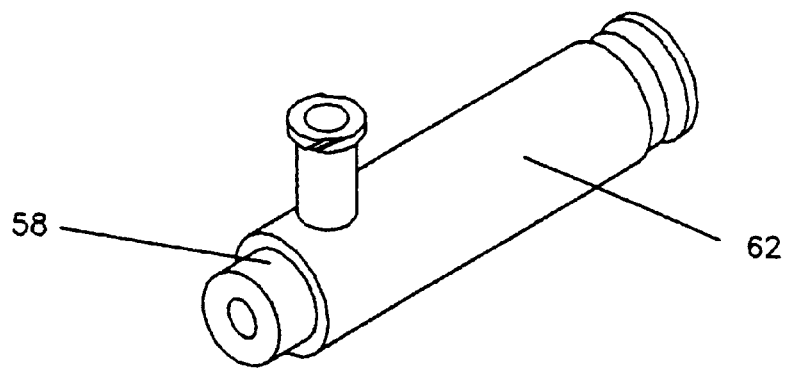
Figure 12:
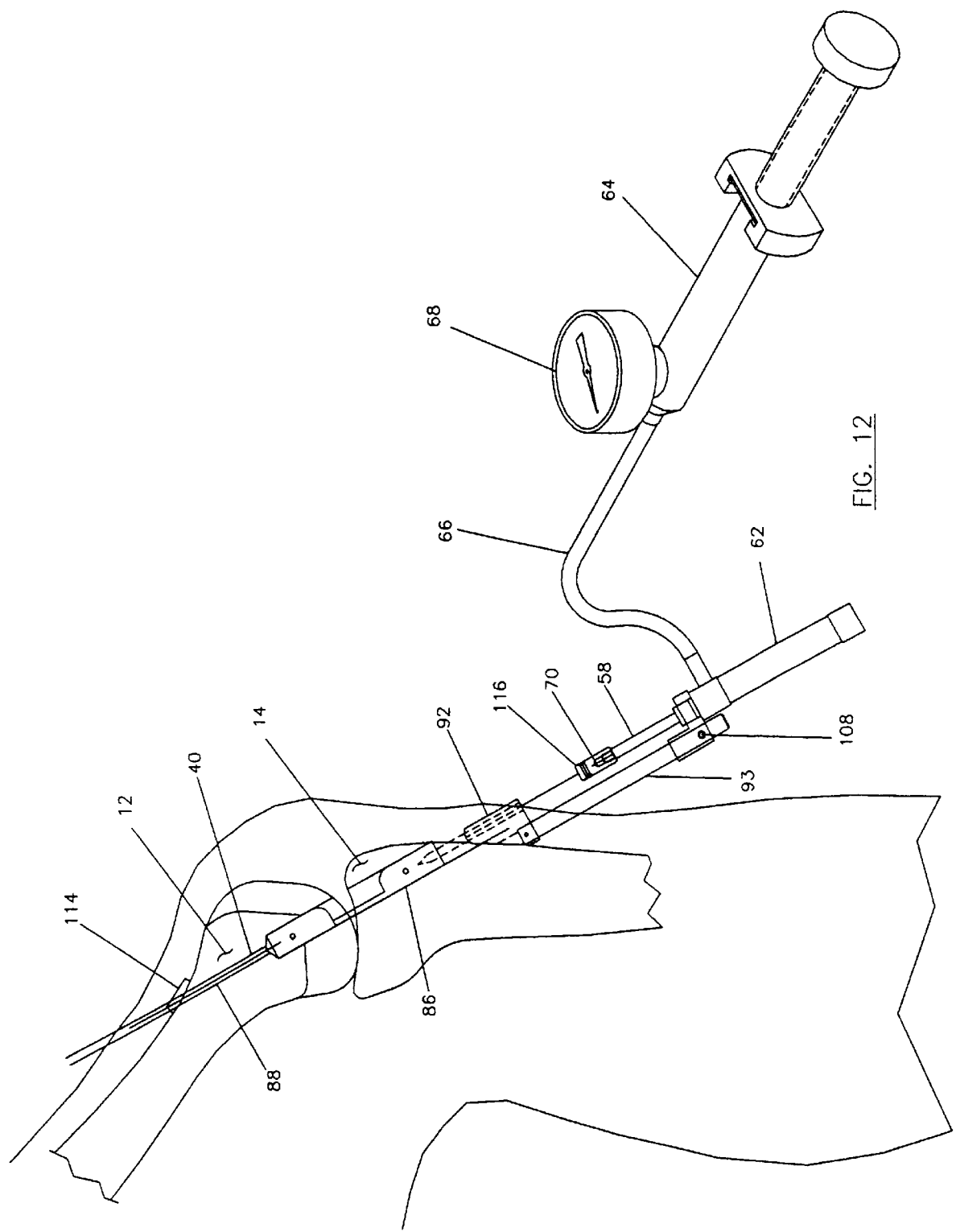
FIG. 12 is a perspective view showing the tensioning device of the present invention operatively positioned on a patient and showing the patient's leg flexed approximately 50° at the knee.

Referring also to FIGS. 5 and 6, the other end of the harvested graft 34 and the slotted end of ruler 22 are mounted on a tanged fixture 54 which includes a removable pin 56, similar in construction to fixture 44. Fixture 54 in turn is treadably mounted onto the distal end of a hydraulically operated piston 58 as will be described in detail hereinafter. The latter is mounted in an aperture in sled 42.

A feature and advantage of the present invention is to accurately set tension on the graft both statically, and while putting the patient's knee through full range of motion. Accordingly, with the graft in place on the tensioning board, sleds 40 and 42 are moved and secured to take up slack. Thereafter, cylinder 62 is pressurized preferably employing a fluid e.g. sterile, water-filled inflation syringe 64 attached to cylinder 62 via a flexible, high pressure tube 66. Inflation syringe 64 preferably comprises a 10 cc LeVeen™ inflator/syringe, available from the Meditech Division of Boston Scientific Corp., which is marked made in accordance with U.S. Pat. No. 4,312,343, the disclosure of which is incorporated herewith by reference, and includes a pressure/vacuum manometer or gauge 68, i.e. in accordance with the teachings of U.S. Pat. No. 5,137,514, which provides a direct readout of pressure applied by cylinder 62 to piston 58 which in turn tensions graft 34. Thus, gauge 68 provides a direct calibrated readout of tension applied to graft 34. Graft 34 is tensioned to approximately the maximum premeasured dimension determined prior to harvesting the graft, i.e. in the range of motion measurements made on the slit tendon as above described. (See FIG. 2A and Table I). The readout on pressure/vacuum manometer gauge 68 is then observed and recorded, and the pressure correlated to the tensioning cylinder cross-sectional area using Table II.

The harvested graft is then put aside temporarily, while the patient's tibia and femur are prepared to accept the graft. Alternatively, another team could prepare the patient's tibia and femur contemporaneously, as follows:

Referring to FIGS. 8–12, cylinder 62 is removed from fixture 42, and fixture 54 is replaced with a suture fixture 70. The latter includes a slot 72 for catching a suture hook as will be described in detail hereinafter. Cylinder 62 is then mounted in a new fixture 74 which includes a hub 76 and screw 78 for slidably fixedly mounting on an elongate rod 80 as will be described hereinafter. In the meanwhile, after initial determination of the location of the drilling site or tunnel 86 is drilled in the tibia.

Another feature and advantage of the present invention involves the ability accurately to align and adjust tension in the ligament graft. In order to accomplish exact alignment, a drilling fixture 92 is fitted with a threaded plug 94 of suitable diameter, i.e. essentially matching tunnel 86, is temporarily installed in tibia tunnel 86. Fixture 92 includes a pair of drilling guide holes 96, 98 running parallel to and in the same plane as plug 94. Two parallel holes, only one of which 100, is shown, are then drilled into the tibia, with the drilling fixture 92 ensuring that holes 100 will be parallel to and in the same plane as tibia tunnel 86. Drilling fixture 92 and plug 94 are then removed, and guide pins 104 and 106 are press fitted into holes 100. Also, at this time the femoral attachment point is cleared of the previous ligament and a "K" wire (not shown) is positioned at the centerpoint of tunner 86, and through the femur, the quadriceps muscle and breaks through the skin. Then a hollow drill is passed over the "K" wire, and the femur tunnel is then drilled. The hollow drill is removed, leaving the "K" wire in place in the femur. A tension element such as a wire cable or suture 110 attached to the proximal end of the "K" wire is then passed through the tunnel openings 86, 88 and the femoral end of graft 34 fixed permanently in tunnel 88 in known manner, e.g. using an interference screw 114, or the like. The tibial end 32 of graft 34 is temporarily clamped or fixed at 116 to fixture 70. Fixture 93 is then slid onto guide pins 104 and 106, and graft tensioning cylinder 62 as will be described in detail below, is then slid onto rod 80, and locked thereon by a set screw 108. As will be appreciated, since holes 96 and 98 and tibia tunnel 86 are parallel and in the same plane, and pins 96 and 98 and rod 80 are all parallel, cylinder 62 will be aligned in fixed position relative to tibia 14, and with its piston 58 aligned parallel to and concentric with tibia tunnel 86.

Yet another feature and advantage of the present invention is to accurately affix and measure tension on the graft both statically, and while putting the knee through full range of motion. To this end, the present invention employs a hydraulic cylinder, attached to the graft for tensioning the graft and for providing a read-out reflective of changes in tension under range of motion. In accordance with a preferred embodiment of the present invention, a fluid inflation syringe 64 is advanced to apply nominal tension, and the patient's knee is then put through a range of motion. The tension is then increased and the patient's knee is then again moved through full range of motion, and changes in tension as indicated on gauge 68 again observed. Tension is again adjusted, i.e. to approximate tension observed as recorded in Table II.

TABLE I

| Patella Tendon Length (Unharvested) | Degrees | Length | |
|---|---|---|---|
| | 0 | | |
| | 45 | | |
| | 90 | | |
| Harvested Tendon on Tension Board | Other Full Length Length | Tension (lbs) | Bars |
| | 1. | | |
| | 2. | | |
| | 3. | | |
| | 4. | | |
| ACL In Place (Endobutton) or (Interference Screw) | Degrees | Tension (lbs) | Bars |
| | 0 | | |
| | 45 | | |
| | 90 | | |

TABLE II

| BARS | ACL LBS. |
|---|---|
| 7.5 | 10. |
| 8 | 10.7 |
| 8.5 | 11.4 |
| 9 | 12 |
| 9.5 | 12.7 |
| 10 | 13.4 |
| 10.5 | 14 |
| 11 | 14.7 |
| 12 | 16 |
| 12.5 | 16.7 |
| 13 | 17.4 |
| 13.5 | 18 |
| 14 | 18.7 |
| 15 | 20 |
| 15.5 | 20.7 |
| 16 | 21.3 |
| 16.5 | 22 |
| 17 | 22.6 |
| 17.5 | 23.3 |
| 18 | 23.9 |

After the graft tension tests are completed, and optimum graft tension confirmed, the tibial end of the graft may then be affixed in known manner, e.g. using a tibial interference screw and the graft is then severed from piston 58 by cutting the loop end of suture 120. Yet another feature and advantage of the present invention is that changes in tension as may result, for example, when the interference screw is inserted can be observed by changes in the readout in gauge 64, and adjustments made. The invention also leaves the surgeon's hands free for setting the interference screw.

From the foregoing, it will be apparent that the method and device of the present invention enable objective skeletal referenced tensioning of ligament grafts in an easy and repeatable manner. As will be appreciated by one skilled in the art, the present invention can be used to tension ligament grafts and also assess resulting joint laxity. To accomplish this, the patient's knee is placed in the desired degree of flexion, and the desired ligament load is developed by advancing the piston of syringe 64 until a desired gauge reading is achieved. Joint laxity can be assessed through manual tests, following the readout on gauge 68, and adjustments made, if necessary, until the observed tensions repeat themselves. The invention also advantageously may be used for tensioning artificial ligament joint repairs, as well as for tensioning ligament joint repairs of joints other than knees.

Various modifications and changes may be made with regard to the foregoing detailed description without departing from the spirit of the invention.

What is claimed is:

1. A method for tensioning a ligament graft within a joint of a patient undergoing ligament surgery, wherein a ligament is harvested from one location of said patient, and moved to and attached to another location within said joint, said method comprising the steps of:

measuring elongation of said ligament while in its original location;

removing said ligament from said patient, temporarily mounting said ligament on a tension board, and measuring tension relative to elongation; and transplanting said ligament in position on said patient, affixing one end thereof, and tensioning the other end to a pre-determined tension as determined on said tension board.

2. A method according to claim 1, wherein elongation of said ligament is measured while moving said patient's joint through a range of motion.

3. A method according to claim 1, wherein said ligament is tensioned with one end affixed to said patient, while moving said joint through a range of motion, so that the maximum tension of said joint approximates the predetermined tension measured on said tension board.

4. A method according to claim 3, wherein ligament tension is monitored while the patient's joint is moved through a range of motion.

5. A method according to claim 3, and including the step of reapplying tension, and again moving said joint through a range of motion until tension repeats itself.

6. A method according to claim 1, wherein said joint comprises a knee, and wherein the ligament is fixed between a patient's tibia and femur, under tension.

* * * * *